United States Patent
Gonzalez et al.

[11] Patent Number: 5,917,326
[45] Date of Patent: *Jun. 29, 1999

[54] GUIDANCE SYSTEM FOR A MOVING PERSON

[75] Inventors: Bernard A. Gonzalez, St. Paul; Richard L. Patten, Minneapolis, both of Minn.

[73] Assignee: Minnesota Mining and Manufacturing Company, St. Paul, Minn.

[*] Notice: This patent is subject to a terminal disclaimer.

[21] Appl. No.: 08/977,351

[22] Filed: Nov. 24, 1997

Related U.S. Application Data

[62] Division of application No. 08/610,786, Mar. 11, 1996, Pat. No. 5,764,060.

[51] Int. Cl.⁶ .............. G01V 3/165; A61F 9/08; E01F 9/04; H01F 1/00
[52] U.S. Cl. .............. 324/326; 324/345; 340/944; 404/9; 404/34; 434/112
[58] Field of Search .............. 324/67, 326, 345; 52/177; 180/167–169; 335/303; 340/905, 944, 957; 404/9, 34; 405/157, 160, 175, 176; 434/112

[56] References Cited

U.S. PATENT DOCUMENTS

| | | |
|---|---|---|
| 1,803,288 | 4/1931 | Adler, Jr. |
| 1,803,289 | 4/1931 | Adler, Jr. |
| 1,803,290 | 4/1931 | Adler, Jr. |
| 1,803,291 | 4/1931 | Adler, Jr. |
| 1,803,292 | 4/1931 | Adler, Jr. |
| 2,493,755 | 1/1950 | Ferrill, Jr. .............. 180/82 |
| 2,999,275 | 9/1961 | Blume, Jr. .............. 18/55 |
| 3,179,918 | 4/1965 | Hoeppel .............. 340/32 |
| 3,254,859 | 6/1966 | Reisch .............. 242/68.5 |
| 3,359,152 | 12/1967 | Blume, Jr. .............. 161/162 |
| 3,493,923 | 2/1970 | Stevens et al. .............. 340/32 |

(List continued on next page.)

FOREIGN PATENT DOCUMENTS

| | | | |
|---|---|---|---|
| 0 260 870 | 3/1988 | European Pat. Off. .......... H01F 1/06 |
| 2 024 021 | 8/1970 | France .............. A61H 3/00 |
| 2382886 | 10/1978 | France .............. A61F 9/08 |
| 2628968 | 9/1989 | France .............. A61F 9/08 |
| 36 16 186 | 11/1987 | Germany .............. A61F 9/08 |
| 37 11 469 | 10/1988 | Germany .............. G08G 1/09 |
| 41 17 872 | 12/1992 | Germany .............. H05C 3/00 |
| 9-328725 | 12/1997 | Japan .............. E01F 9/04 |

OTHER PUBLICATIONS

"Magnetic sensors to direct blind"; London Financial Times; Sep. 9, 1994.

"Device for Guiding the Blind"; Course Materials, Practicing Law Insitute (PLI), New York, New York, Apr. 1995.

Stauffer; "IVHS Introductory System"; Honeywell, Inc.; Jul. 30, 1993.

Watanabe et al.; "Ferrites—Proceedings of the ICF 3"; Sep.–Oct. 1980, Japan.

Lenz; "A Review of Magnetic Sensors"; Proceedings of the IEEE, vol. 78, No. 6, Jun. 1990.

(List continued on next page.)

*Primary Examiner*—Gerard Strecker
*Attorney, Agent, or Firm*—Peter L. Olson

[57] ABSTRACT

The guidance system of the invention includes at least two spaced, permanently magnetized regions that each produce a magnetic field. The two permanently magnetized regions can be provided at either side of another region that produces a magnetic field of less intensity than the permanently magnetized regions, and in one embodiment, the former region produces no magnetic field. The system may also include portable means for detecting the magnetic fields produced by the permanently magnetized regions, and that sensor may be mounted to a cane for use by a person. In another embodiment, the permanently magnetized regions contrast with either each other or the region that produces a magnetic field of less intensity, or have different surface characteristics, or both.

15 Claims, 3 Drawing Sheets

U.S. PATENT DOCUMENTS

| | | | |
|---|---|---|---|
| 3,575,255 | 4/1971 | Wickstrom | 180/98 |
| 3,609,678 | 9/1971 | Fayling | 340/32 |
| 3,642,087 | 2/1972 | Sampey | 180/98 |
| 3,668,624 | 6/1972 | Spaulding | 340/32 |
| 3,714,625 | 1/1973 | Fayling | 340/32 |
| 3,753,223 | 8/1973 | Fayling | 340/32 |
| 3,787,839 | 1/1974 | Fayling | 340/381 |
| 3,878,367 | 4/1975 | Fayling et al. | 235/61.12 |
| 3,927,393 | 12/1975 | Fayling | 340/149 |
| 4,185,265 | 1/1980 | Griffin et al. | 340/32 |
| 4,219,092 | 8/1980 | Richter | 180/169 |
| 4,299,874 | 11/1981 | Jones et al. | 428/143 |
| 4,497,722 | 2/1985 | Tsuchida et al. | 252/62.54 |
| 4,600,883 | 7/1986 | Egli et al. | 324/207 |
| 4,623,282 | 11/1986 | Allen | 405/157 |
| 4,634,977 | 1/1987 | Lenz et al. | 324/244 |
| 4,715,743 | 12/1987 | Schmanski | 404/9 |
| 4,742,300 | 5/1988 | Lenz et al. | 324/244 |
| 4,767,237 | 8/1988 | Cosman et al. | 405/157 |
| 5,039,979 | 8/1991 | McClive | 340/438 |
| 5,187,475 | 2/1993 | Wagener et al. | 340/870 |
| 5,227,221 | 7/1993 | Hedblom | 428/172 |
| 5,303,669 | 4/1994 | Szekely | 116/205 |
| 5,316,406 | 5/1994 | Wyckoff | 404/12 |
| 5,347,456 | 9/1994 | Zhang et al. | 364/424 |
| 5,764,060 | 6/1998 | Gonzalez et al. | 324/326 |

OTHER PUBLICATIONS

Lenz et al.; "A High–Sensitivity Magnetoresistive Sensor"; IEEE Solid–State Sensor and Actuator Workshop; Jun. 1990.

Lenz et al.; "Magnetic materials characterization using a fiber optic magnetometer"; J. Appl. Phys. 57(1), Apr. 15, 1985.

Lenz et al.; "Fiber Optic Magnetometers for Field Mapping"; 1983 International Geoscience and Remote Sensing Symposium; Aug./Sep., 1983.

Ramsey et al.; "Feasibility Study of IVHS Drifting out of Lane Alert System"; Innovations Deserving Exploratory Analysis (IDEA) Program—Intelligent Vehicle–Highway Systems (IVHS); Sep. 1994.

GUIDANCE SYSTEM FOR A MOVING PERSON

This is a division of application Ser. No. 08/610,786 filed Mar. 11, 1996, now U.S. Pat. No. 5,764,060.

TECHNICAL FIELD

The invention relates to a mobile object guidance system, and particularly to a cane-based guidance system for guiding visually impaired individuals along a desired path.

BACKGROUND OF THE INVENTION

Individuals who are visually impaired face many obstacles to everyday navigation. For example, such individuals often must use public transportation, such as a subway system, for travel. Those systems may be difficult to navigate without the benefit of adequate sight, and thus it is desirable to provide a guidance system that is inexpensive, reliable, and durable.

One type of conventional guidance system includes a longitudinally extensive, permanently magnetized region, such that a sensor mounted in a cane can emit a sound when the cane is swept across the region. Although these systems have utility, one disadvantage is that they can be unipolar, meaning that they have only one polarity and can emit only one signal as the cane sweeps over the magnetic field. Also, conventional systems that are not based on permanent magnets typically require comparatively expensive sensors to detect the signal.

Another disadvantage of several conventional guidance systems is that they cannot be easily applied to an existing surface. Some systems include, for example, magnets embedded in a surface to activate a sensor. This arrangement is inconvenient to install in an existing surface, because the surface may have to be at least partially destroyed to embed the magnet. Also, if the magnets are permanently adhered to or embedded within the surface, they cannot easily be repositioned to indicate a new pathway.

Yet another disadvantage of some conventional guidance systems is that they may not provide the most effective guidance for sighted, but visually-impaired, individuals. That is, systems designed to aid persons who are completely blind may not have other useful attributes that would aid a sighted, but visually-impaired person. In view of these and other disadvantages associated with conventional guidance systems, it is desirable to provide a new guidance system having a variety of available features.

SUMMARY OF THE INVENTION

The term "guidance system," as used herein, means a system that provides information to a user through one of the user's senses. Thus, the guidance system of the present invention includes portions that are permanently magnetized, to enable a magnetic sensor to provide a signal to a user. It may also be visually contrasted, to provide visual information to a user, and may be tactually contrasted, to provide tactile information to a user. These features may also be incorporated into a guidance system for other mobile objects, such as a forklift or other robotic apparatus.

In one embodiment, the inventive system includes at least two spaced, permanently magnetized regions that each produce a magnetic field. The two permanently magnetized regions can be provided at either side of another region that produces a magnetic field of less intensity than the permanently magnetized regions, and in one embodiment, the former region produces no magnetic field. The system may also include portable means for detecting the magnetic fields produced by the permanently magnetized regions, and that sensor may be mounted to a cane for use by a person. In another embodiment, the permanently magnetized regions contrast with either each other or the region that produces a magnetic field of less intensity, or have different surface characteristics, or both.

DETAILED DESCRIPTION OF THE INVENTION

Figure 1:
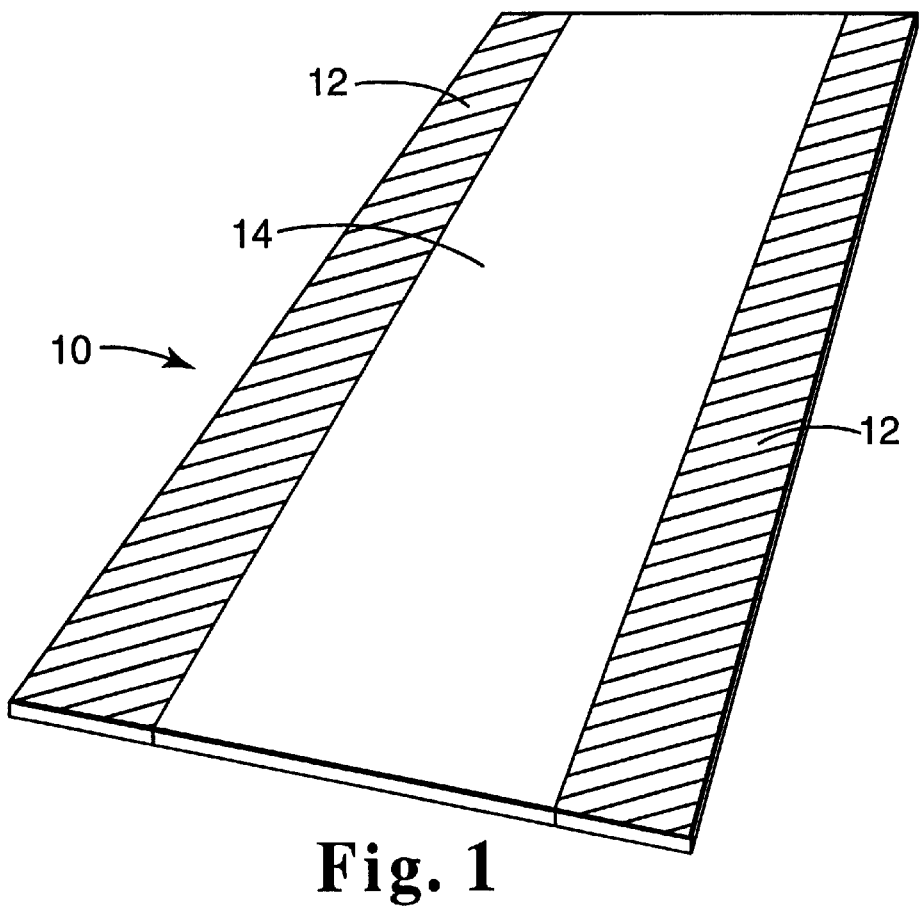
FIG. 1 is a perspective view of one embodiment of the guidance system of the present invention.

The inventive guidance system allows a mobile object, such as a person, to gain information from the system either by touch, by sound, by sight, or by some combination thereof As shown in FIG. 1, the system includes spaced, permanently magnetized regions, each of which produce a magnetic field that can be detected by a sensor. When the sensor detects the fields, it notifies the user of the location of the sensor. Alternatively, the magnetic field sensor can trigger a tactile alarm, such as a vibrating mechanism, which can be connected to the sensor directly or wirelessly. Also, the permanently magnetized regions can be tactually contrasted either from each other, or from an intermediate region that produces a magnetic field of lesser intensity, to permit a user to gain information tactually. Lastly, the system also provides visual contrast either between the permanently magnetized regions, or between the permanently magnetized regions and other regions. Each of these features (magnetic, tactile, and visual contrast) may be used independently, or in combination with one or both of the other features. The effect is to provide a versatile guidance system that may be tailored to provide the features desired by the installer and the users.

I. General Operation of the System

Figure 2:
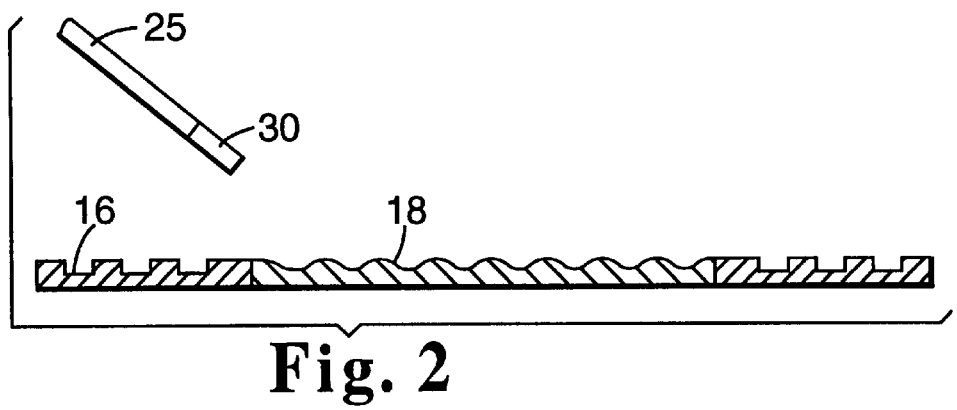
FIG. 2 is a cross-sectional view of a second embodiment of the guidance system of the present invention.

A preferred embodiment of the inventive guidance system is illustrated in FIG. 1. As shown therein, the system 10 includes spaced permanently magnetized regions 12 separated by a region 14 that produces a magnetic field of lesser intensity than regions 12. Region 14 will be referred to herein as the "weaker field region." The permanently magnetized regions are preferably, though not necessarily, identical, and are also preferably different from the weaker field region in magnetism, texture, and visual appearance. A user may use a cane 25 as shown in FIG. 2, to detect the differences. in texture between the permanently magnetized and weaker field regions. That cane may also have a magnetic field sensor 30, as shown in FIG. 2, so that the user may also detect the differences in magnetic field between the permanently magnetized and weaker field regions. Lastly, the visual appearance of at least one of the regions should contrast sufficiently with the appearance of the other two regions to permit persons with reduced vision to perceive the difference. These features are described individually below.

The present inventors have discovered, among other things, that spaced regions having certain characteristics separated by a weaker field having other characteristics is more easily perceived than is a single region. This is believed to be true because spaced, permanently magnetized regions of particular dimensions provide more signals per cane sweep than a single region, and stronger signals at particular distances. This makes the strip much more easily detectable than other systems having a single region.

II. Magnetic Contrast

The magnetized regions are preferably permanently magnetized, meaning that they produce a magnetic field, whereas the weaker field region is preferably magnetically inactive. A portable sensor detects the presence and direction of the magnetic field at each side of the path, and the absence of a magnetic field (or a weaker magnetic field) in the middle of the path, and provides signals to the user. The signal may be an audio signal, a vibratory signal, a visual signal, or any other means of indicating to the user that the sensor has detected a magnetic field.

The permanently magnetized regions are made to produce a magnetic field of sufficient intensity to permit detection by the sensor. Magnetic fields of approximately 0.5 gauss at a distance of 15.25 cm (6 in) are desired, although fields of greater or lesser intensity may be desirable for certain applications. The regions are preferably unpowered, though powered regions may be provided if desired. Also, the regions preferably emit a continuous signal, rather than periodic signals, to minimize confusion for the user as to whether he has left the desired path, or is only between successive signals. Also, the regions may be made to produce magnetic fields of alternating polarity, so that the net field is essentially undetectable at a distance.

Three factors most directly influence the detectability of the magnetic signal: area (the size of the region over which the magnetic material is placed), power (the strength of the magnetic material) and arrangement (how the magnetic material is oriented). Experiments have shown that the magnetic regions are more easily detected when they are placed over a large area. However, it is impractical to place magnetic regions over an entire floor or hallway, and thus a compromise is necessary. One manner in which to achieve sufficient area is to supply a magnetized tape or strip that can be applied in continuous form, and also to provide mats (made, perhaps, from several strips of tape) near obstacles, doors, and the like.

More powerful tapes are more easily detected than less powerful tapes, and one way to provide more powerful tapes is to use a wider or thicker tape. Although a wider or thicker tape can be detected at greater distances than can a narrower or thinner tape, the latter is actually more detectable at closer range than is the former. This effect is shown in the following Table One, which illustrates magnetic field strength (in gauss) as a function of tape width and measurement distance above the tape. The tape used to make these measurements was made as described in Section V., below, and measured approximately 5.08 cm (2 in) wide, 2.0 mm (0.07 in) thick, and 152.4 cm (5 ft) long.

TABLE One

| Distance above tape | Tape Width | | | |
|---|---|---|---|---|
| | 2.54 cm (1 in) | 5.08 cm (2 in) | 10.16 cm (4 in) | 20.32 cm (8 in) |
| 2.54 cm (1 in) | 7.44 | 9.41 | 7.60 | 4.51 |
| 5.08 cm (2 in) | 2.22 | 3.78 | 4.75 | 3.82 |

TABLE One-continued

| Distance above tape | Tape Width | | | |
|---|---|---|---|---|
| | 2.54 cm (1 in) | 5.08 cm (2 in) | 10.16 cm (4 in) | 20.32 cm (8 in) |
| 7.62 cm (3 in) | 1.02 | 1.90 | 2.93 | 3.06 |
| 10.16 cm (4 in) | 0.59 | 1.12 | 1.90 | 2.39 |
| 15.24 cm (6 in) | 0.26 | 0.52 | 0.95 | 1.47 |
| 20.32 cm (8 in) | 0.15 | 0.29 | 0.58 | 0.96 |
| 25.4 cm (10 in) | 0.10 | 0.19 | 0.37 | 0.66 |
| 30.48 cm (12 in) | 0.07 | 0.13 | 0.26 | 0.48 |

As shown in Table One, narrower tapes have a more pronounced transition from strong magnetic field to weak magnetic field as sensing distance increases. For example, a 2.54 cm wide tape has a magnetic field at 30.48 cm that is less than 1% as strong as the same tape at 2.54 cm, whereas the field strength of the 20.32 cm wide tape only decreases to 11% of its initial field strength at the same distance. Because transitions between a strong magnetic field and a weak (or no) field are most easily detected, a narrower tape is preferred to a wider one for most applications. More specifically, because the tape should be detectable at about 12.7 cm (5 in), and should be most detectable at about 2.54 cm (1 in), the 5.08 cm (2 in) wide tape is a preferred width.

Finally, with regard to the arrangement of the magnetically active regions, a series of tests were conducted with 5.08 cm (2 in) wide strips spaced from each other by either 0.0 cm (0 in), 5.08 cm (2 in), 10.16 cm (4 in), and 15.24 cm (6 in), and field strength measurements were taken at 2.54 cm (1 in) above the strips in 8 locations relative to the two strips, and at 10.16 cm (4 in) above the strips in 3 locations. The greatest transition between large magnetic field and small magnetic field occurred with strips of opposite polarities spaced apart by at least approximately 5.08 cm (2 in).

In view of the foregoing considerations, one embodiment of the present invention includes two 5.08 cm (2 in) wide strips of magnetically active tape spaced 10.16 cm (4 in) apart. This product could be provided in roll form, wherein the roll has a total width of approximately 20.32 cm (8 in).

The sensor used to detect the magnetic field may be of any suitable type. Generally, the sensor should be inexpensive, durable, and sufficiently sensitive to detect the magnetic field produced by the permanently magnetized regions. The sensor should be matched to the magnetic field produced by the permanently magnetized regions, to enable the former to detect the latter reliably. Another beneficial attribute of the present invention is the ability to use a relatively low-cost sensor, particularly if the sensor will be used in close proximity to the magnetic regions. One preferred sensor is a hall-effect sensor, one suitable type of which is available from the Honeywell MicroSwitch Company of Minneapolis, Minn. under the designation SS495A. The sensor may be mounted at the end of a cane or a walker, in or on a shoe, or in any other convenient location, subject only to the ability of the sensor to detect the magnetic field, and to detect differences in magnetic field.

III. Tactile Contrast

Tactile contrast between the permanently magnetized and weaker field regions may be provided in several different ways. FIG. 2 illustrates regions that are tactually contrasted. By making the permanently magnetized regions tactually contrasted with the weaker field region, the user can determine whether the cane is moving along the desired path, or is beginning to depart from the desired path.

Tactile contrast may be provided by a series of longitudinal or transverse grooves, bumps, or any other suitable structure. In FIG. 2, for example, a set of aligned, longitudinal grooves 16 with square cross-sections are formed in the permanently magnetized regions 12, and a set of aligned, longitudinal grooves 18 with more rounded cross-sections are formed in the weaker field region 14. The grooves are typically 1.3 mm (0.05 in) deep and 3.3 mm (0.13 in) wide, which permits easy cleaning and provides a skid-resistant surface. Another surface that provides skid resistance and a different texture consists of granules approximately 0.77 mm (0.03 in) in diameter spread randomly on a top-coated surface and thereby bonded to the substrate.

Figure 3:
FIG. 3 is a cross-sectional view of a third embodiment of the guidance system of the present invention.

A different embodiment of the present invention is shown in FIG. 3, in which no tactile contrast is provided, because the tape 10a will be used under carpet, for example.

In a preferred embodiment described herein, comprising two 5.08 cm (2 in) wide magnetically active strips separated by a 10.16 cm (4 in) inactive region, the outer strips are highly textured (as with pavement marking tapes available from the Minnesota Mining and Manufacturing Company (3M) under the designation 380 series STAMARK™ pavement marking tape, and the middle region should be of lesser texture but still be skid-resistant (as with 3M's flat, reflective, skid-resistant marking tapes).

IV. Visual Contrast

Regions that are visually contrasted are typically desirable so that users with limited vision can identify the path defined by those regions. Visual contrast between the permanently magnetized regions and the lesser field regions may be provided by color or pattern. Although colors such as black and white may be used, a yellow-green color (550 nanometer wavelength) contrasted with a black boundary is believed to provide maximum visual contrast. Moreover, because increased brightness provides increased contrast, which is desirable, it is preferred that certain of the colors selected be as bright as possible. One way to increase brightness, and thus contrast, is to add fluorescence, and thus the yellow-green color described above may be fluorescent in one embodiment.

When spaced magnetic regions are separated by an intermediate region, it is preferred that the intermediate region is yellow-green and that the spaced magnetic regions are black. In other embodiments, various standard or fluorescent colors may be used, as well as patterns, such as checkerboard patterns, logos, alphanumeric symbols, and arrows indicating a desired path direction. Tape 10a, as shown in FIG. 3, need not have visual contrast if it will be used where it cannot be seen, such as below a carpet.

In a preferred embodiment described herein, comprising two 5.08 cm (2 in) wide magnetically active strips separated by a 10.16 cm (4 in) inactive region, the outer strips are black and the central inactive region is fluorescent green-yellow having a wavelength of about 550 nanometers.

V. Construction and Application

The permanently magnetized and weaker field regions may be made of any suitable material, including such things as plastic and metal. A preferred material for the permanently magnetized regions is available from the Traffic Control Materials Division of 3M under the experimental designation "SmartTape," because it is durable, it produces a detectable magnetic field, and it may be made to produce a tactually and visually contrasted region. A preferred material for the weaker field region is available from 3M under the designation STAMARK™ 380 or 385, because it costs less than the material used to make the permanently magnetized regions, yet it too is durable and can be molded and colored.

To make the permanently magnetized regions, several conventional processes may be used. A preferred process is to compound the following materials (all parts are by weight) in a Banbury-type internal mixer.

| Masterbatch | |
|---|---|
| Paracril B | 100.0 |
| Chlorez 700S | 70.0 |
| Paroil 140 LV | 5.0 |
| Stearic Acid | 0.5 |
| Vanstay SC | 0.5 |
| Santowhite Crystals | 1.0 |
| PE Minifiber 13038F | 20.0 |
| PET 6-3025 fibers | 10.0 |
| Magnetic Particles | |
| Barium hexaferrite P-235 | 950.0 |
| total weight | 1157 |

In the foregoing list, Paracril™ B is a medium acrylonitrile content nitrile rubber available from Uniroyal Chemical Company of Akron, Ohio; Chlorez™ 700S is a solid chlorinated paraffin available from Dover Chemical Corporation of Dover, Ohio; Paroil 140 LV is a liquid chlorinated paraffin available from Dover Chemical Corporation; Stearic Acid is a process aid available from Humko Chemical Division of Witco Chemical Corporation of Memphis, Tenn.; Vanstay™ SC is a "chelating agent" type stabilizer available from R. T. Vanderbilt Company, Inc. of Norwalk, Conn. Santowhite™ Crystals are an antioxidant available from Monsanto Chemical Company of St. Louis, Mo.; PE Minifiber 13038F is a high density polyethylene fiber available from Mini Fibers, Inc. of Johnson City, Tenn.; PET 6-3025 fibers are 0.635 cm (0.25 in) by 3d polyester fibers available from Mini Fibers, Inc.; and Barium hexaferrite P-235 is a magnetic pigment available from Arnold Engineering Co. of Norfolk, Nebr.

When the temperature of the mix reaches 146° C. (295° F), the mix is dropped from the mixer onto a two-roll rubber mill. The material is sheeted off the rubber mill and fed through a two-roll calendar to yield a sheet of material having a thickness of approximately 1.4 mm (0.055 in).

The sheet of material was embossed according to the process described in U.S. Pat. No. 5,227,221 (col. 2, lines 47–65) to provide a conformable magnetic sheet having a plurality of protrusions projecting from one major surface. The embossed sheet had a thickness of about 0.5 mm (0.02 in) in the valleys between the protrusions, and a thickness of about 1.6 mm (0.063 in) at the top of the protrusions. A discontinuous layer of liquid particle bond material was applied to the top and sides of the protrusions of the embossed sheet using the process described in U.S. Pat. No. 5,227,221. The particle bond material was the same as the polyurethane bead bond of U.S. Pat. No. 5,227,221 (col. 4, lines 20–39), with the exception that the pigment dispersion was made with the following composition:

| Particle Bond Pigment Dispersion | | |
|---|---|---|
| Ingredient | % (by weight) | Function |
| methyl isobutyl ketone | 7.04 | solvent |
| zinc 2-ethylhexanoate | 3.52 | catalyst |
| Stan-Tone 10 EPX03 | 41.55 | white pigment dispersion |
| Stan-Tone 25 EPX01 | 3.52 | red pigment dispersion |
| Stan-Tone 90 EPX04 | 44.37 | black pigment dispersion |

Stan-Tone 10 EPX03 is a white pigment dispersion in a diglycidyl ether of bisphenol A epoxy resin. Stan-Tone 25 EPX-1 is a red pigment dispersion in a diglycidyl ether of bisphenol A epoxy resin. Stan-Tone 90 EPX04 is a black pigment dispersion in a diglycidyl ether of bisphenol A epoxy resin. Each is available from the Harwick Chemical Corporation of Akron, Ohio under the listed designation.

The surface of the particle-bond-material-coated protrusions was sprinkled with durable black spherical anti-skid particles of the type available from Carbo Ceramics of New Iberia, La. under the designations CARBOLITE and CARBOPROP. The particles were applied so as to partially embed them in the liquid particle bond material. The liquid particle bond material was solidified by passing the sheet through an oven at a temperature of about 175° C. (350° F.) for approximately 10 minutes of residence time, as described in U.S. Pat. No. 5,227,221.

A layer of rubber resin pressure sensitive adhesive with a thickness of about 125 micrometers (0.005 in) was laminated to the bottom of the sheet. The sheet felt similar to conformable pavement marking tapes and quite similar to those of STAMARK™ 380 Series pavement marking tape and STAMARK™ 385 Series Non-Reflective Joint Cover Tape available from 3M. The sheet was visually similar to STAMARK™ 385 series tape except that the non-particle coated regions between the projections were dark purplish-brown in color instead of black.

In general, the permanently magnetized and weaker field regions may also be of any suitable width and thickness, and may either be continuous or segmented, though the former is preferred. For example, the weaker field region may be approximately 25 to 180 mm (1.0 to 7.0 in) wide, and approximately 2 mm (0.08 in) thick. The permanently magnetized regions may each be approximately 10 to 75 mm (0.5 to 3.0 in) wide, with the same thickness as the weaker field region. The outermost edges of the regions are preferably feathered, to permit a wheeled vehicle to traverse the regions more easily. The separation between the permanently magnetized regions is believed to be important for the reasons previously described, and the separation distance is preferably twice the width of a single permanently magnetized region. Although continuous regions are preferred, to insure that a user doesn't mistake a discontinuity in the regions for an incorrect path, segmented regions may be used where appropriate.

The present invention may be used indoors or outdoors, and may be applied either under substrates such as carpet, tile, or concrete, or applied to the top of those or other surfaces. For example, to provide a path in an existing subway station, the system may be applied to existing concrete floors along the desired paths, and secured to those floors using a suitable adhesive. For an office, it may be more desirable to provide the system beneath carpet (and thus without the tactile and visual contrast features), which may be easily accomplished by making the regions as thin as possible. In new construction, the system may be buried beneath concrete. In such a case, the weaker field region may be modified to be only a mesh, or some structure sufficient to maintain a uniform distance between the permanently magnetized regions.

Additional features may also be built into the present guidance system. For example, where a path divides, the tactile,. magnetic, and visual features of the regions may be different for each part of the new path to indicate that a division has occurred. The right-hand path, for example, might have transverse channels, a higher magnetic field, and a checkerboard pattern, whereas the left-hand path might have longitudinal channels, a lower magnetic field, and a straight-line pattern. Different texture patterns may also be used to contrast the regions from each other. The regions may have an adhesive (either pressure sensitive or heat-activated) thereon to enable attachment to a surface. If the adhesive is a pressure sensitive adhesive, it may be of the type that permits repositioning, and may be protected by a removable liner. The various regions may also be conformable, both to conform to irregularities in the surface to which the regions are attached, as well as to permit the regions to be curved.

Figure 4:
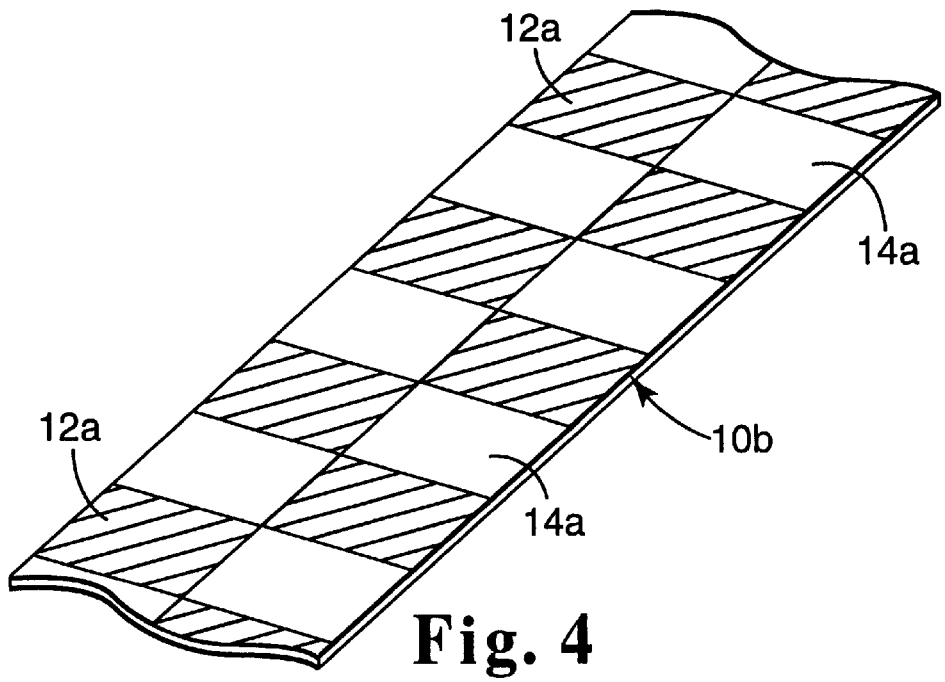
FIG. 4 is a perspective view of a fourth embodiment of the guidance system of the present invention.

FIG. 4 illustrates another embodiment of the system of the present invention, in which the spaced magnetically active regions 12a alternate with lesser field regions 14a along each tape 10b.

Figure 5:
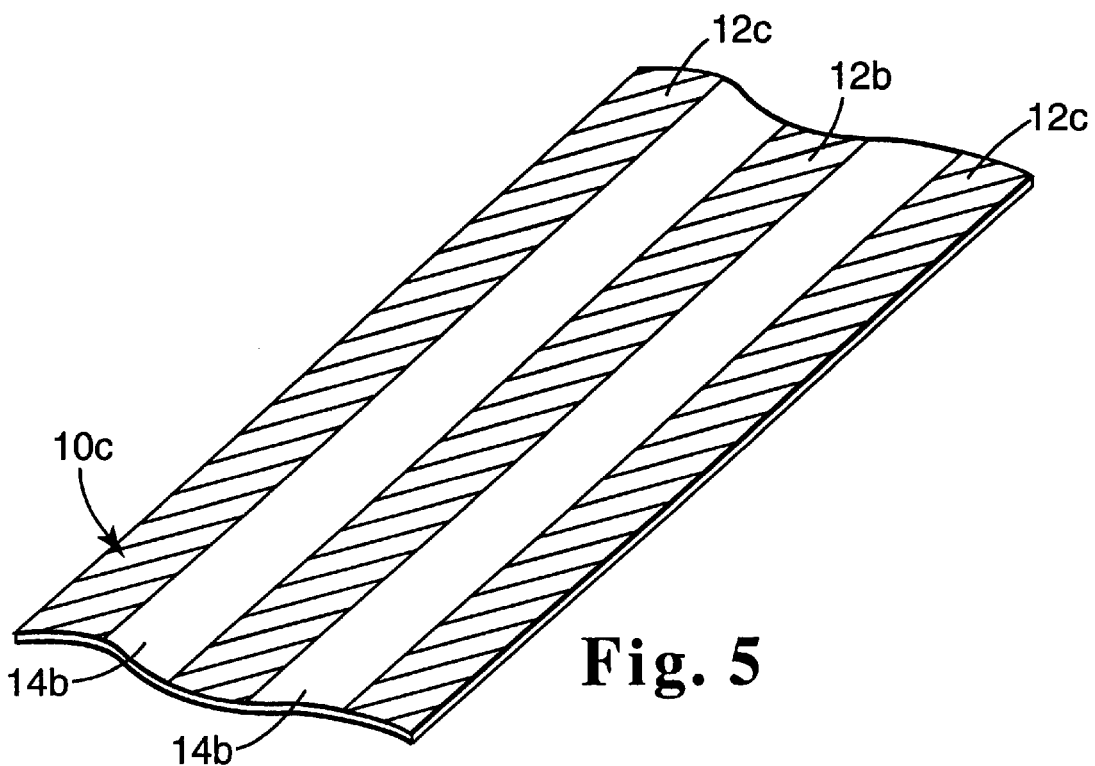
FIG. 5 is a perspective view of a fifth embodiment of the guidance system of the present invention.

Multiple weaker field regions and permanently magnetized regions may also be provided in a single tape 10c, as shown in FIG. 5. There, central permanently magnetized region 12b is flanked by weaker field regions 14b, which are in turn flanked by permanently magnetized regions 12c.

Figure 6:
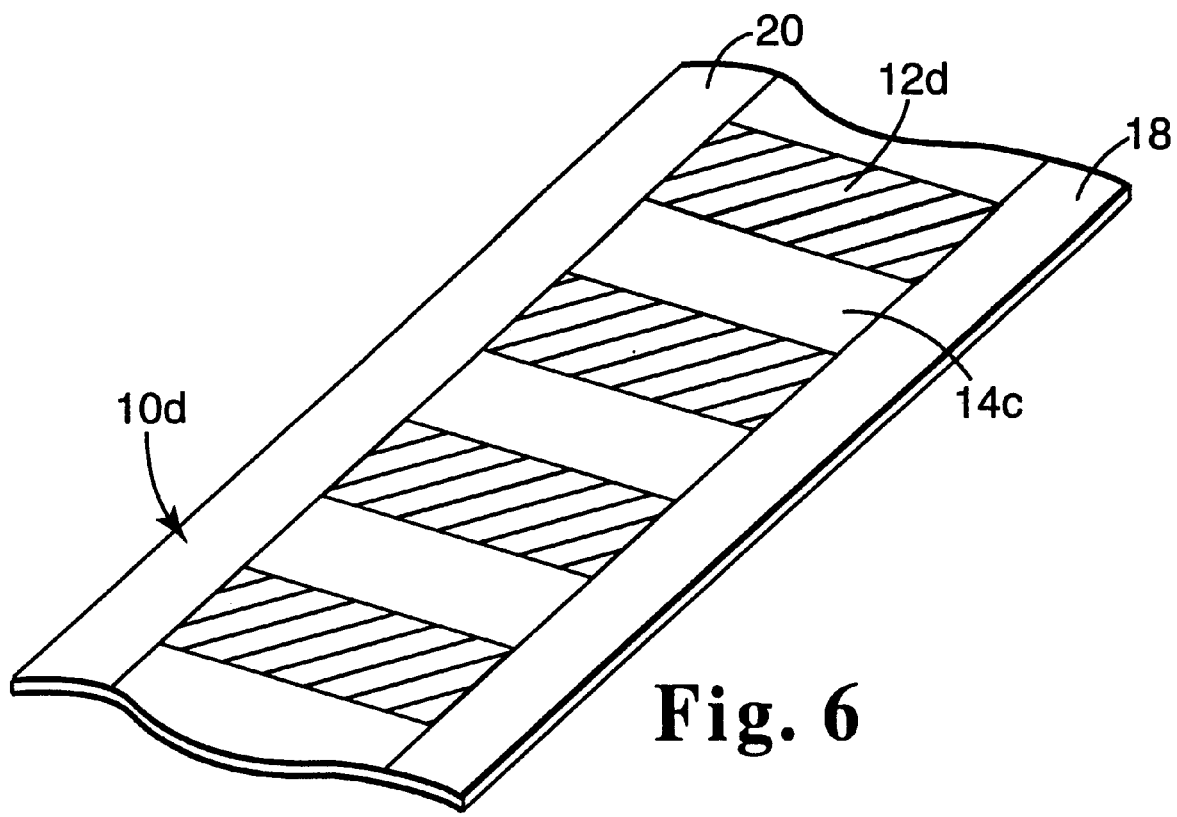
FIG. 6 is a perspective view of a sixth embodiment of the guidance system of the present invention.

FIG. 6 illustrates yet another embodiment, in which permanently magnetized regions 12d and weaker field regions 14c are arranged transversely in alternating relationship along the length of the illustrated tape 10d. Additional regions 20 may be provided along the outer edge of the permanently magnetized and weaker field regions 12d and 14c, if desired, and may have the attributes of either or neither of those types of regions.

VI. Experimental Results

The guidance system of the present invention was tested with eleven subjects to assess four guidance functions: stopping, change in path direction, straight-line guidance, and locating. The subjects were typical of persons who seek guidance because of visual limitations, such as limited field of view, blurry vision, night blindness, and blindness in one eye. The subjects were provided with a cane having a sensor in the tip. When the cane was moved near a guidance tape, described below, the sensor emitted a tone through a speaker in the handle of the cane. The cane, including the sensor tip, was 160 cm (5.25 ft) long.

The guidance tape was placed beneath a carpet that was sufficiently thick to prevent visual or tactile identification, and the room lighting was extinguished. The tape consisted of three stripes each measuring 5.1 cm (2.0 in) wide, each placed parallel to each other at a distance of 5.1 cm (2.0 in) apart.

With regard to the four tested guidance functions, stopping is important because it is enables a subject to avoid a hazard. Stopping was measured by providing a segment of tape described above at a predetermined location along the hallway, and instructing the subjects to stop when they detected the tape. Change in path direction was measured by placing the tape in a path that turned left 4.2 m (14 ft) after the starting point. Subjects were not told which way the path turned, but were instructed to follow the path. Straight-line guidance was tested by placing the tape in a straight line, and then instructing each subject to following the tape twice: once with the sensor turned off, and once with the sensor turned on. The subject traversed the carpet until he or she crossed a line 4.8 m (16 ft) from the starting point, at which point the deviation from a straight line was measured. Finally, the locating function is important because it enables a subject to find a particular room, door, elevator, or other location. To test the locating function, one segment of the tape was placed under a doorway, and subjects were instructed to move along the hallway until they identified the door. There were a total of eight doors in the hallway.

The system of the present invention was effective in helping the subjects to navigate straight lines and corners, and to locate a particular place. Specifically, in the stopping test all of the subjects stopped in front of the tape, at an average of about 168 cm (5.5 ft) in front of the tape. In the change of path direction test, all of the subjects correctly followed the path to the left. In the straight line navigation test, the subjects deviated an average of 60 cm (1.97 feet) from the straight line with the sensor turned off, and an average of 14.6 cm (0.48 ft) from the straight line with the sensor activated. In the locating test, all eleven subjects correctly located the marked doorway.

Suitable uses for the present invention are manifold. It may be used in offices, schools, homes, public facilities, hotels, and hospitals, and can be used to mark not only desired paths but also structures such as staircases, emergency exits, bathrooms, drinking fountains, windows, and doors. Another use is to mark an edge or a boundary between two regions, such as the entrance to a parking lot from a sidewalk.

Although the present invention has been described with respect to several illustrative embodiments, the scope of the present invention is defined not by those embodiments, but by the following claims.

We claim:

1. A guidance system for a person moving through an environment, the system comprising at least two spaced, longitudinally extending magnetized strips for placement along a path of travel for guiding the person along the path, each of said strips including regions having magnetic and coloration features along the length of the strip that are different from the environment and thereby perceptible to the person.

2. The system of claim 1, wherein said system further comprises at least one weaker field region.

3. The guidance system of claim 2, wherein the strips are secured in adjacent relationship to provide a continuous tape.

4. The guidance system of claim 2, wherein said weaker field region produces no magnetic field.

5. The guidance system of claim 1, further comprising a portable means for detecting the magnetic fields produced by the magnetized regions.

6. The guidance system of claim 5, wherein said detecting means further comprises means for providing an indication of the location of the detecting means relative to the magnetized regions.

7. The guidance system of claim 6, wherein said detecting means is mounted to a cane.

8. The guidance system of claim 1, wherein the magnetized and weaker field regions are unpowered.

9. The guidance system of claim 1, wherein at least one strip includes a layer of adhesive for bonding the strip to a surface.

10. The guidance system of claim 9, wherein said adhesive is a pressure sensitive adhesive.

11. The guidance system of claim 10, wherein said strip with pressure sensitive adhesive is repositionable.

12. The guidance system of claim 10, wherein said pressure sensitive adhesive has a removable liner attached thereto.

13. The guidance system of claim 1, wherein the strips are conformable to irregularities in a surface to which the strips are applied.

14. The guidance system of claim 1, wherein said magnetized regions are arranged such that they have opposite polarities.

15. The guidance system of claim 1, wherein the coloration feature is provided by a fluorescent color.

* * * * *